US006066757A

United States Patent [19]
Tanaka et al.

[11] Patent Number: 6,066,757
[45] Date of Patent: May 23, 2000

[54] STILBENE COMPOUND AND PROCESS FOR PRODUCING SAME

[75] Inventors: Chiaki Tanaka, Shizuoka-ken; Masaomi Sasaki, Susono; Tomoyuki Shimada, Shizuoka-ken, all of Japan

[73] Assignee: Ricoh Company, Ltd., Tokyo, Japan

[21] Appl. No.: 09/008,954

[22] Filed: Jan. 20, 1998

Related U.S. Application Data

[62] Division of application No. 08/823,694, Mar. 25, 1997, abandoned, which is a division of application No. 08/416,988, Apr. 5, 1995, Pat. No. 5,641,598.

[30] Foreign Application Priority Data

| | | | |
|---|---|---|---|
| Apr. 6, 1994 | [JP] | Japan | 6-068513 |
| Oct. 28, 1994 | [JP] | Japan | 6-265299 |

[51] Int. Cl.[7] .......... C07C 69/017; C07C 43/02; C07C 39/21

[52] U.S. Cl. .......... 560/138; 560/130; 560/139; 560/142; 560/146; 568/586; 568/707

[58] Field of Search .......... 560/255, 238, 560/130, 138, 139, 142, 146; 568/586, 707

[56] References Cited

FOREIGN PATENT DOCUMENTS 61-014642 1/1986 Japan .

OTHER PUBLICATIONS

Patent & Trademark Office English Translation of JP 61–14642, published Jan. 1986.

Webster's New World Dictionary, Third College Edition No Month Provided (1988), p. 1317.

*Primary Examiner*—Rosalynd Keys
*Attorney, Agent, or Firm*—Oblon, Spivak, McClelland, Maier & Neustadt, P.C.

[57] ABSTRACT

A stilbene compound is disclosed which has the following general formula (I):

(I)

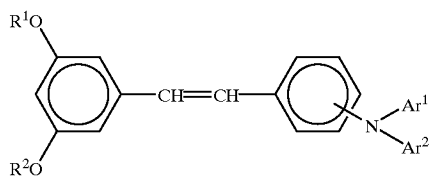

wherein $R^1$ and $R^2$ each stand for hydrogen, an alkyl group or an acyl group and $Ar^1$ and $Ar^2$ each stand for a monovalent homocyclic aromatic group. The stilbene compound may be incorporated into a photoconducting layer of an electrophotographic photoconductor as a charge transporting material. A process for the production of the stilbene compound is also disclosed.

7 Claims, 6 Drawing Sheets

STILBENE COMPOUND AND PROCESS FOR PRODUCING SAME

CROSS-REFERENCE TO RELATED APPLICATIONS

This application is a divisional of Ser. No. 08/823,694, filed Mar. 25, 1997, now abandoned, which is a divisional of Ser. No. 08/416,988, filed Apr. 5, 1995, now U.S. Pat. No. 5,641,598.

BACKGROUND OF THE INVENTION

1. Field of the Invention

This invention relates to EL novel stilbene compound useful as an organic photoconductive material for use in electrophotography and to a process for the production thereof. The present invention is also directed to an electrophotographic photoconductor.

2. Description of Prior Art

Electrophotographic photoconductor include a laminate-type one in which a charge generating layer containing a charge generating pigment capable of generating charge carriers upon being irradiated with light and a charge transport layer containing a charge transport material capable of accepting and transporting the charge carriers from the charge generating layer are laminated on an electroconductive support.

A variety of charge transport materials have thus far been proposed, such as poly-N-vinylcarbazole compounds, triphenylamine compounds (U.S. Pat. No. 3,180,730), benzidine compounds (U.S. Pat. No. 3,265,496) and stilbene compounds (Japanese Published Unexamined patent applications. Nos. 58-198,425, 58-198,043, 58-189,145 and 58-190,953). As precursors for polymeric charge transport materials, dihydroxy compounds are proposed in U.S. Pat. No. 4,801,517 and Japanese Published Unexamined patent applications Nos. 1-105,260 and 3-294,251.

While the above-mentioned electrophotographic photoconductors show good characteristics, the conventional photoconductors cannot fully meet with various requirements in the electrophotographic process.

SUMMARY OF THE INVENTION

It is, therefore, an object of the present invention to provide a novel stilbene compound useful as an organic photoconductive material for use in electrophotography.

Another object of the present invention is to provide a stilbene compound of the above-mentioned type which can afford an electrophotographic photoconductor having an excellent durability and an excellent resistance to thermal or mechanical shocks.

It is a further object of the present invention to provide a process which can easily produce a stilbene compound with a high yield.

It is yet a further object of the present invention to provide an electrophotographic photoconductor which can be easily manufactured at relatively low costs and which has an excellent durability and an excellent resistance to thermal or mechanical shocks.

In accomplishing the foregoing object, the present invention provides a stilbene compound having the following general formula (I):

(I)

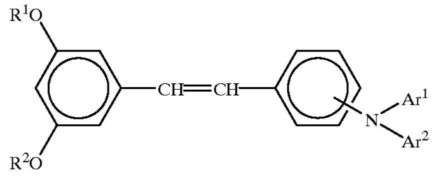

wherein $R^1$ and $R^2$ stand, independently from each other, for a hydrogen atom, an alkyl group which may have one or more substituents or an acyl group which may have one or more substituents and $Ar^1$ and $Ar^2$ stand, independently from each other, for a monovalent homocyclic aromatic group which may have one or more substituents.

In another aspect, the present invention provides a process for the production of a stilbene compound having the following general formula (I):

(I)

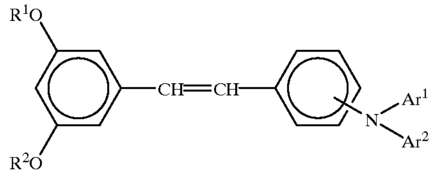

wherein $R^1$ and $R^2$ stand, independently from each other, for a hydrogen atom, an alkyl group which may have one or more substituents or an acyl group which may have one or more substituents and $Ar^1$ and $Ar^2$ stand, independently from each other, for a monovalent homocyclic aromatic group which may have one or more substituents, said process comprising reacting an aldehyde compound having the following general formula (III):

(III)

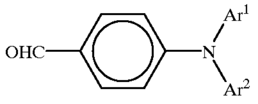

wherein $Ar^1$ and $Ar^2$ have the same meaning as above, with a phosphorus compound having the following general formula (IV):

(IV)

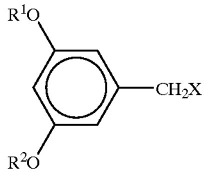

wherein $R^1$ and $R^2$ have the same meaning as above, X represents $-P^+(R^3)_3Y^-$ where $R^3$ represents a phenyl group or a lower alkyl group and Y represents a halogen atom or $-PO(OR^4)_2$ where $R^4$ represents a lower alkyl group.

The present invention also provides a process for the production of a stilbene compound having the following general formula (I):

(I)

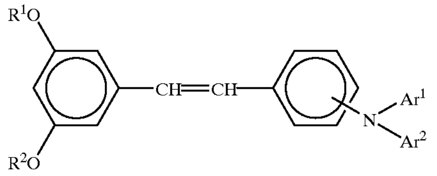

wherein $R^1$ and $R^2$ stand, independently from each other, for a hydrogen atom, an alkyl group which may have one or more substituents or an acyl group which may have one or more substituents and $Ar^1$ and $Ar^2$ stand, independently from each other, for a monovalent homocyclic aromatic group which may have one or more substituents, said process comprising reacting an amino compound having the following general formula (V):

(V)

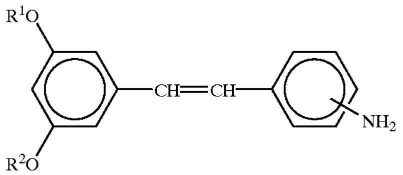

wherein $R^1$ and $R^2$ have the same meaning as above, with at least one of two halides having the following formulas (VI):

$Ar^1Z$ and $Ar^2Z$ (VI)

wherein $Ar^1$ and $Ar^2$ have the same meaning as above and Z represents a halogen atom.

In a further aspect, the present invention provides an electrophotographic photoconductor comprising an electroconductive substrate and a photosensitive layer provided on said substrate and containing at least one stilbene compound expressed by the following general formula (VIII):

(VIII)

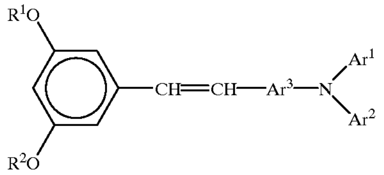

wherein $R^1$ and $R^2$ stand, independently from each other, for a hydrogen atom, an alkyl group which may have one or more substituents or an acyl group which may have one or more substituents with the proviso that at least one of $R^1$ and $R^2$ represents a hydrogen atom or an acyl group, $Ar^1$ and $Ar^2$ stand, independently from each other, for a monovalent homocyclic aromatic group which may have one or more substituents and $Ar^3$ stands for a divalent homocyclic aromatic group which may have one or more substituents.

In the present specification, the preferred meaning of the terms "halogen atom", "alkyl group", "lower alkyl group", "homocyclic aromatic group" and "acyl group" used for identifying the symbols $R^1$–$R^4$, $Ar^1$–$Ar^3$, Y and Z are as follows:

The halogen atom is preferably fluorine, chlorine, bromine or iodine;

The alkyl group is a straight chain or branched chain alkyl group having preferably 1–12, more preferably 1–9, most preferably 1–4 carbon atoms. When the alkyl group is recited as being able to have one or more substituents, the substituent may be a phenyl group or a substituted phenyl group having a C1–C4 alkyl group or a phenyl group as a substituent. Examples of the alkyl groups include methyl, ethyl, n-propyl, i-propyl, t-butyl, s-butyl, n-butyl, i-butyl, benzyl, 4-methylbenzyl and 4-phenylbenzyl groups;

The lower alkyl group is a straight chain or branched chain alkyl group having 1–8, preferably 1–4 carbon atoms;

The homocyclic aromatic group may be a non-condensed-ring aromatic group such as a phenyl, biphenyl or terphenyl group, or a condensed-ring aromatic group such as a pentalenyl, indenyl, naphthyl, azulenyl, heptalenyl, biphenylenyl, as-indacenyl, fluorenyl, s-indacenyl, acenaphthylenyl, pleiadenyl, acenaphthenyl, phenalenyl, phenanthryl, anthryl, fluoranthenyl, acephenanthrylenyl, aceanthrylenyl, triphenylenyl, pyrenyl, chrysenyl or naphthacenyl group. When the homocyclic aromatic croup is recited as being able to have one or more substituents, the substituent may be a halogen atom, an alkyl group, a phenyl group or a substituted phenyl group having a C1–C4 alkyl group or a phenyl group as a substituent; and The acyl group is represented by —CO—$R^5$ where $R^5$ is an alkyl group, a phenyl group or a substituted phenyl group having a C1–C4 alkyl group or a phenyl group as a substituent.

BRIEF DESCRIPTION OF THE DRAWINGS

Other objects, features and advantages of the present invention will become apparent from the detailed description of the preferred embodiments which follows, when considered in light of the accompanying drawings, in which.

DETAILED DESCRIPTION OF THE PREFERRED EMBODIMENTS OF THE INVENTION

Figure 1:
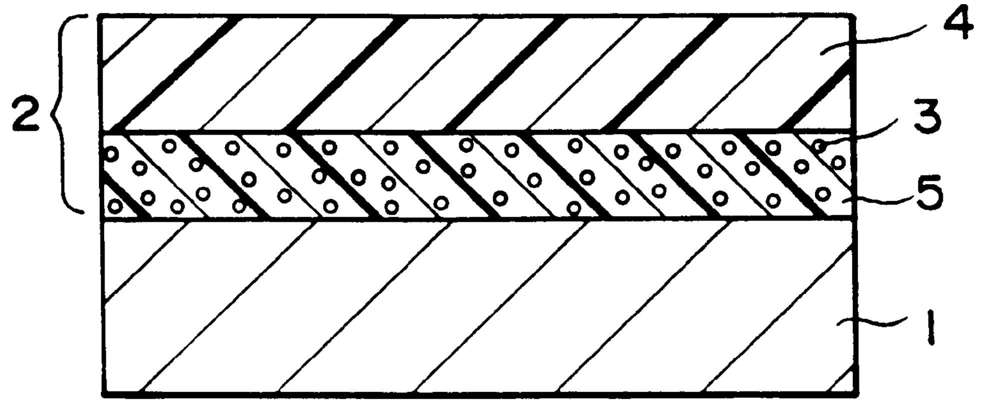
FIG. 1 is a cross-sectional view schematically showing an embodiment of an electrophotographic photoconductor according to the present invention.

In the above formula (I), $R^1$ and $R^2$ stand, independently from each other, for (a) a hydrogen atom, (b) an alkyl group, preferably a lower alkyl group such as a methyl group, an ethyl group, a propyl group or a butyl group, which may have one or more substituents such as a phenyl group or (c) an acyl group, preferably an acetyl group, a propionyl group or a butynyl group, which may have one or more substituents such as a phenyl group. In the formula (I), $Ar^1$ and $Ar^2$ stand, independently from each other, for a monovalent homocyclic aromatic group, such as a phenyl group, a biphenyl group, a naphthyl group, anthryl group or a pyrenyl group, which may have one or more substituents such as an alkyl group, e.g. a lower alkyl group, or a halogen atom, e.g. a chlorine atom.

The stilbene compound of the above formula (I) may be obtained by reacting an aldehyde of the above formula (III)

with a phosphorus compound having the formula (IV). The reaction is preferably performed in the presence of a basic catalyst in a solvent. The basic catalyst may be, for example, an alkali metal hydroxide such as sodium hydroxide and potassium hydroxide; an alkali metal hydride such as sodium hydride; an alcolate such as phenyllithium, sodium methoxide or potassium t-butoxidephenyl lithium; or sodium amide. Illustrative of suitable solvents are methanol, ethanol, isopropanol, butanol, 2-methoxyethanol, 1,2-dimethoxyethane, bis(2-methoxydiethyl)ether, dioxane, tetrahydrofuran, benzene, toluene, xylene, dimethylsulfoxide, N,N-dimethylformamide, N-methylpyrrolidone or 1,3-dimethyl-2-imidazolidinone. Particularly preferred is the use of dimethylsulfoxide, N,N-dimethylformaminde or like polar solvent. The suitable reaction temperature may be determined according to the stability of the solvent against the catalyst, the reactivity of the reactants (compounds of the formulas (III) and (IV)), and the activity of the catalyst and is generally in the range of from room temperature to about 100° C., preferably from room temperature to about 80° C., when a polar solvent is used.

The compound of the formula (I) may also be produced by reacting an amino compound having the above formula (V) with one or two halides having the above formulas (VI). The reaction is preferably performed in the presence of copper powder, a copper oxide or a copper halide and in the further presence of an alkaline substance with or without a solvent at a temperature of 150–250° C. in the atmosphere of an inert gas such as nitrogen. The alkaline substance may be, for example, sodium hydroxide, potassium hydroxide, sodium carbonate, potassium carbonate or sodium hydrogen carbonate and is used in an amount sufficient to neutralize a hydrogen halide produced in situ by the condensation of the compounds (V) and (VI). Illustrative of suitable solvents are nitrobenzene, dichlorobenzene, quinoline, N,N-dimethylformaldehyde, dimethylsulfoxide, N-methylpyrrolidone, 1,3-dimethyl-2-imidazolidinone, tetrahydrofuran and carbon disulfide. The amino compound of the formula (V) is a known compound and may be prepared by a method as disclosed in Japanese Published Unexamined Patent Application No. 58-65440.

The stilbene compound of the above formula (I) in which $R^1$ and $R^2$ do not simultaneously represent a hydrogen atom is further subjected to a dealkylation or deacylation treatment to convert at Least one of the $R^1O$ and $R^2O$ groups into a hydroxyl group and to yield a dihydroxystilbene compound of the following formula (II) or a monohydroxystilbene compound (VII):

(II)

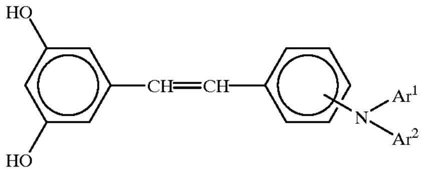

-continued (VII)

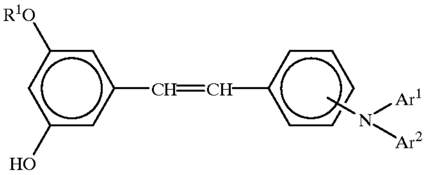

wherein $R^1$, $Ar^1$ and $Ar^2$ are as defined above.

The dealkylation may be carried out by cleaving the $R^1$—O and/or $R^2$—O bond with an acid or a base. The acid may be, for example, hydrogen bromide, hydrogen iodide, trifluoroacetic acid, a hydrochloride of pyridine, hydrochloric acid, magnesium iodide etherate, aluminum chloride, aluminum bromide, boron tribromide, boron trichloride or boron triiodide. The base may be, for example, potassium hydroxide, lithium diphenylphosphide or sodium thiolate. The dealkylation may be generally performed using a solvent such as dichloromethane, tetrahydrofuran, N,N-dimethylformaide, pyridine or butanol at a temperature of from room temperature to about 200° C.

The deacylation may be carried out by cleaving the $R^1$—O and/or $R^2$—O bond with an acid or a base, such as with hydrochloric acid, salfuric acid, sodium hydroxide or potassium hydroxide at a temperature of from room temperature to about 200° C. using a solvent such as methanol, ethanol, isopropanol, butanol, 2-methoxyethanol, 1,2-dimethoxyethane, bis(2-methoxydiethyl)ether, dioxane, tetrahydrofuran, benzene, toluene, xylene, dimethylsulfoxide, N,N-dimethylformamide, N-methylpyrrolidone or 1,3-dimethyl-2-imidazolidinone.

The present invention also provides an electrophotographic photoconductor which includes an electroconductive substrate and a photosensitive or photoconductive layer provided on the substrate and containing at least one stilbene compound of the above formula (VIII). The stilbene compound (VIII) may be used as a photoconductive material for any known electrophotographic photoconductor but is suitably utilized as a charge transport material for a photoconductor having a laminate-type photosensitive layer provided on an electroconductive substrate.

One such electrophotographic photoconductor is illustrated in FIG. 1. Designated as 1 is an electroconductive substrate or support on which a photosensitive layer 2 is provided. The photosensitive layer includes a lower, charge generating layer 5 containing a charge generating material 3 and an upper, charge transport layer 4 containing at least one stilbene compound of the formula (VIII). If desired, the location of the charge transport layer 4 may be changed so that the charge generating layer 5 represents an upper layer. In this case, it is preferred that the charge generating layer 5 be overlaid with a protecting layer. The construction and fabrication of the electrophotographic photoconductor are well known in the art and details thereof are not described here.

Specific examples of the stilbene compounds of the formula (VIII) are shown in Table 1.

| Compound No. | $R^1$ | $R^2$ | $Ar^1$ | $Ar^2$ | $Ar^3$ |
|---|---|---|---|---|---|
| 1 | H | H | 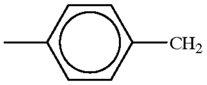 | 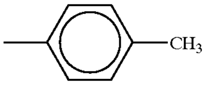 | 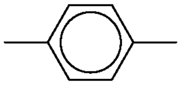 |
| 2 | H | H | 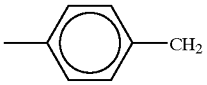 | 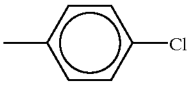 | 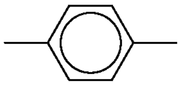 |
| 3 | H | H | 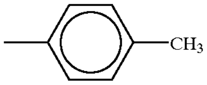 | 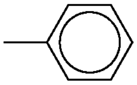 | 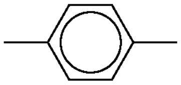 |
| 4 | H | H | 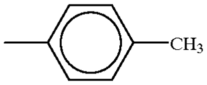 | 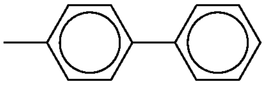 | 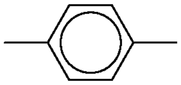 |
| 5 | H | H | 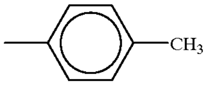 | 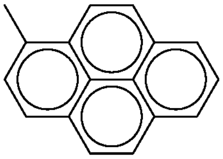 | 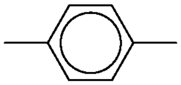 |
| 6 | H | H | 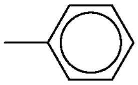 | 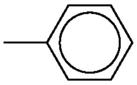 | 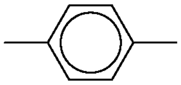 |
| 7 | $CH_3$ | H | 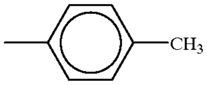 | 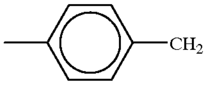 | 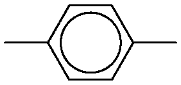 |
| 8 | $CH_3$ | H | 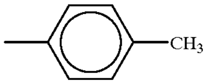 | 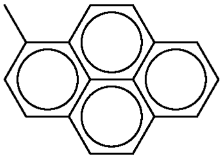 | 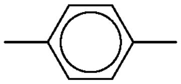 |
| 9 | $CH_3$ | H | 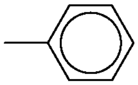 | 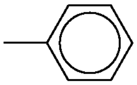 | 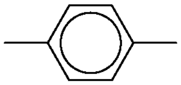 |
| 10 | $COCH_3$ | H | 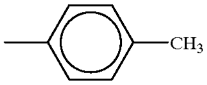 | 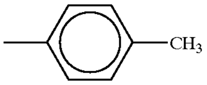 | 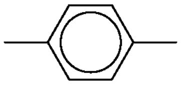 |
| 11 | $COCH_3$ | H | 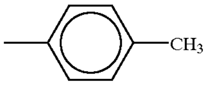 | 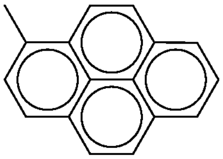 | 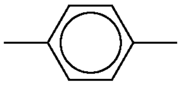 |
| 12 | $COCH_3$ | H | 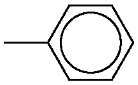 | 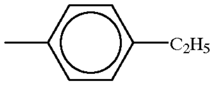 | 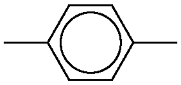 |

-continued
| Compound No. | $R^1$ | $R^2$ | $Ar^1$ | $Ar^2$ | $Ar^3$ |
|---|---|---|---|---|---|
| 13 | $COCH_3$ | $CH_3$ | 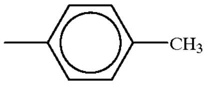 | 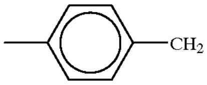 | 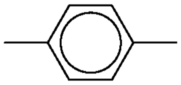 |
| 14 | $COCH_3$ | $CH_3$ | 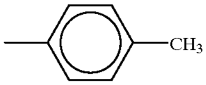 | 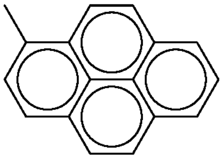 | 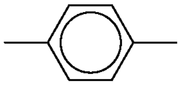 |
| 15 | $COCH_3$ | $CH_3$ | 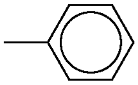 | 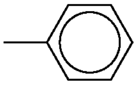 | 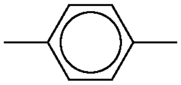 |
| 16 | $COCH_3$ | $COCH_3$ | 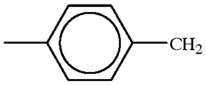 | 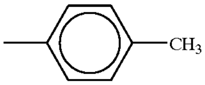 | 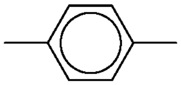 |
| 17 | $COCH_3$ | $COCH_3$ | 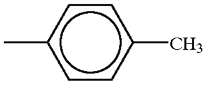 | 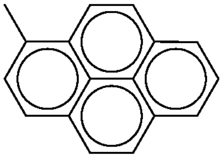 | 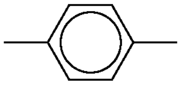 |
| 18 | $COCH_3$ | $COCH_3$ | 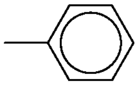 | 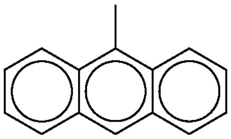 | 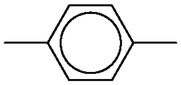 |
| 19 | H | H | 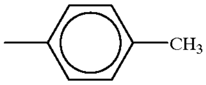 | 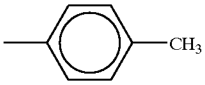 | 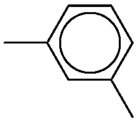 |
| 20 | H | H | 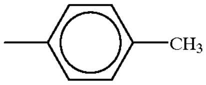 | 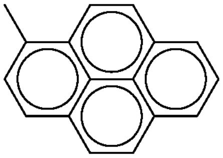 | 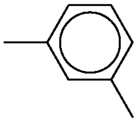 |
| 21 | H | H | 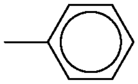 | 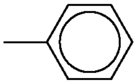 | 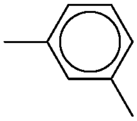 |
| 22 | $CH_3$ | H | 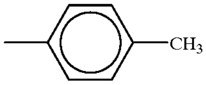 | 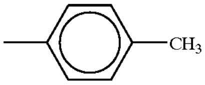 | 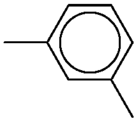 |

-continued
| Compound No. | $R^1$ | $R^2$ | $Ar^1$ | $Ar^2$ | $Ar^3$ |
|---|---|---|---|---|---|
| 23 | $CH_3$ | H | 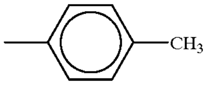 | 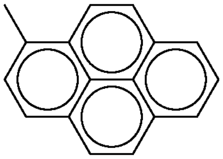 | 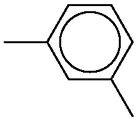 |
| 24 | $CH_2$ | H | 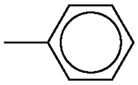 | 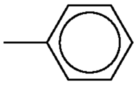 | 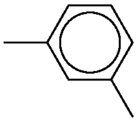 |
| 25 | $COCH_3$ | H | 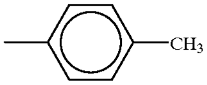 | 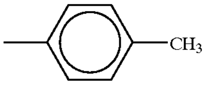 | 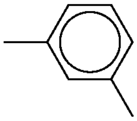 |
| 26 | $COCH_3$ | H | 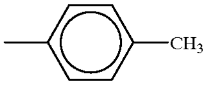 | 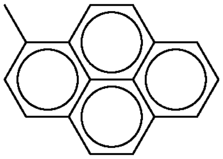 | 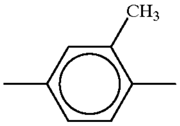 |
| 27 | 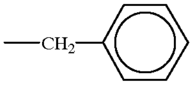 | H | 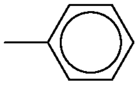 | 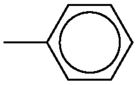 | 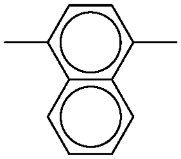 |
| 28 | $CH_2$ | $COCH_3$ | 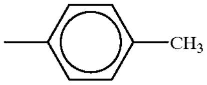 | 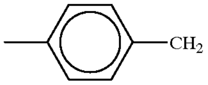 | 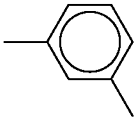 |
| 29 | $CH_3$ | $COCH_3$ | 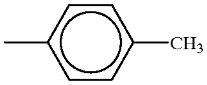 | 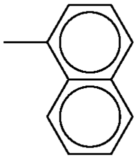 | 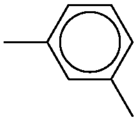 |
| 30 | $CH_3$ | $COCH_3$ | 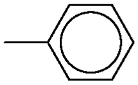 | 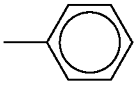 | 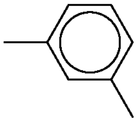 |
| 31 | $COCH_3$ | $COCH_3$ | 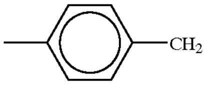 | 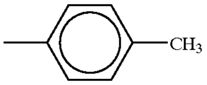 | 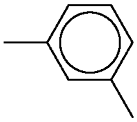 |

-continued

| Compound No. | $R^1$ | $R^2$ | $Ar^1$ | $Ar^2$ | $Ar^3$ |
|---|---|---|---|---|---|
| 32 | $COCH_3$ | $COCH_3$ | 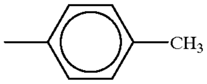 | 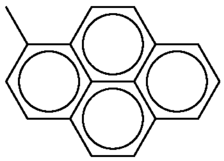 | 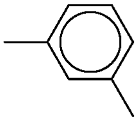 |
| 33 | $COCH_3$ | $COCH_3$ | 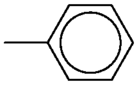 | 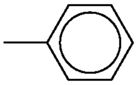 | 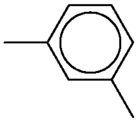 |
| 34 | H | H | 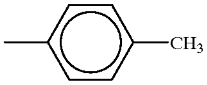 | 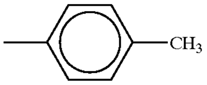 | 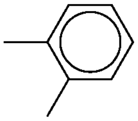 |
| 35 | $C_3H_5$ | H | 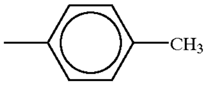 | 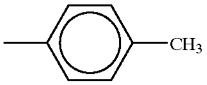 | 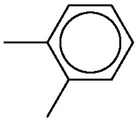 |
| 36 | $COCH_3$ | H | 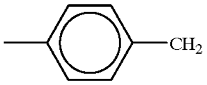 | 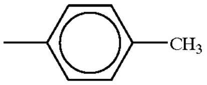 | 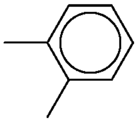 |
| 37 | $CH_3$ | $COC_3H_5$ | 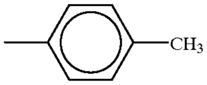 | 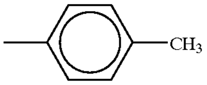 | 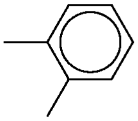 |
| 38 | $COCH_3$ | $COCH_3$ | 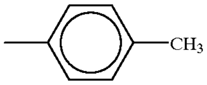 | 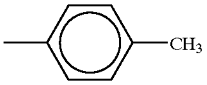 | 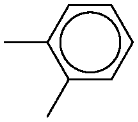 |

The following examples will further illustrate the present invention.

EXAMPLE 1

Synthesis of 4'-bis(4-methylphenyl)amino-3,5-dimethoxy-stilbene:

Into 60 g of p-iodotoluene were added 4.11 g (16.1 mmol) of 3,5-dimethoxy-4'-aminostilbene, to which 2.05 g (32.2 mmol) of copper powder and 8.90 g (64.4 mmol) of potassium carbonate were further added. The resulting mixture was then reacted at 209° C. for 6 hours with stirring in a nitrogen gas stream. Thereafter, the reaction mixture was cooled to 50° C. and filtered together with sellaite. The filtrate was distilled for the removal of the solvent and the residue was chromatographed on a silica gel column using toluene as an elution liquid. From the eluate, 5.07 g (yield: 72.3%) of a product was obtained as a white yellow powder. This was recrystallized from an ethyl acetate-ethanol mixed solvent to give 4.58 g (yield: 65.3%) of 4'-bis(4-methylphenyl)amino-3,5-dimethoxystilbene as white yellow crystals in the form of plates having a melting point of 134.0–135.0° C. The elementary analysis gave the following results:

| | C (%) | H (%) | N (%) |
|---|---|---|---|
| Calculated* | 82.73 | 6.71 | 3.22 |
| Found | 82.80 | 6.75 | 3.11 |

*as $C_{30}H_{29}NO_2$

Figure 2:
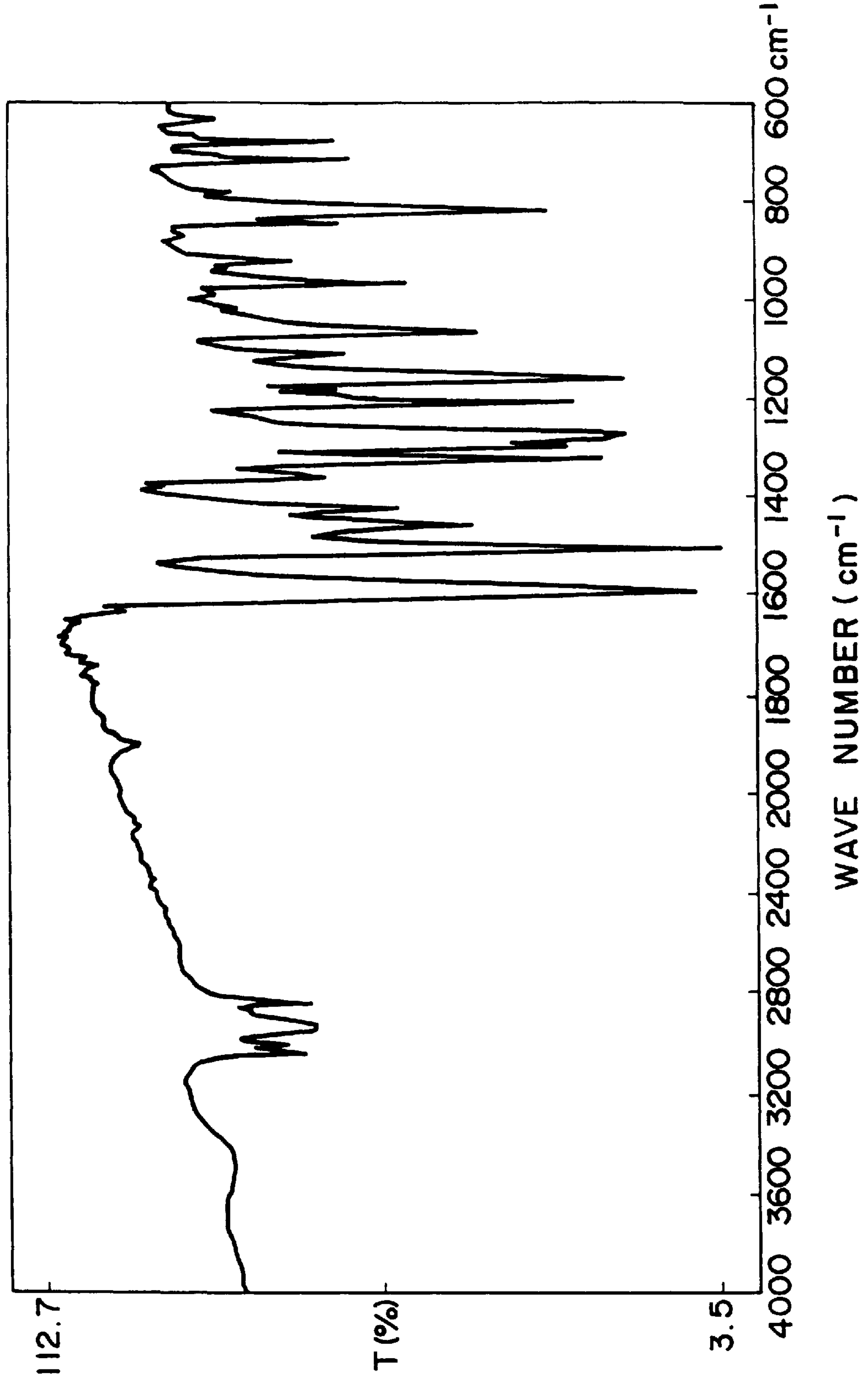
FIGS. 2 through 6 are infrared spectra of stilbene compounds obtained in the examples.

FIG. 2 shows an infrared spectrum of the stilbene product with the KBr method, indicating δCH (transolefin) at 965 $cm^{-1}$.

EXAMPLE 2

Synthesis of 4'-bis(4-methylphenyl)amino-3,5-dihydroxy-stilbene (Compound No. 1):

4'-bis(4-methylphenyl)amino-3,5-dimethoxy-stilbene (4.36 g (10.0 mmol)) obtained in Example 1 and 14.02 g of 90% sodium thioethylate were added into 40 ml of N,N-dimethylformamide which had been treated with molecular sieves 4A and the resulting mixture was reacted at 145–155° C. for 12 hours with stirring in a nitrogen gas stream. The reaction mixture was then cooled to room temperature and poured in 500 ml of ice water, followed by addition of concentrated hydrochloric acid to make the liquid acidic. This was extracted with ether and the extract was distilled to remove the solvent. The residue was chromatographed on a silica gel column using a 5:1 (vol/vol) toluene/ethyl acetate mixed solvent as an elution liquid. From the eluate, 1.65 g (yield: 40.5%) of 4'-bis(4-methylphenyl)amino-3,5-dihydroxystilbene(was obtained as yellow needle-like crystals having a melting point of 161.3° C. (TG-DTA heat absorption peak). The elementary analysis gave the following results:

| | C (%) | H (%) | N (%) |
|---|---|---|---|
| Calculated* | 82.53 | 6.18 | 3.44 |
| Found | 82.80 | 6.35 | 3.36 |

*as $C_{28}H_{25}NO_2$

Figure 3:
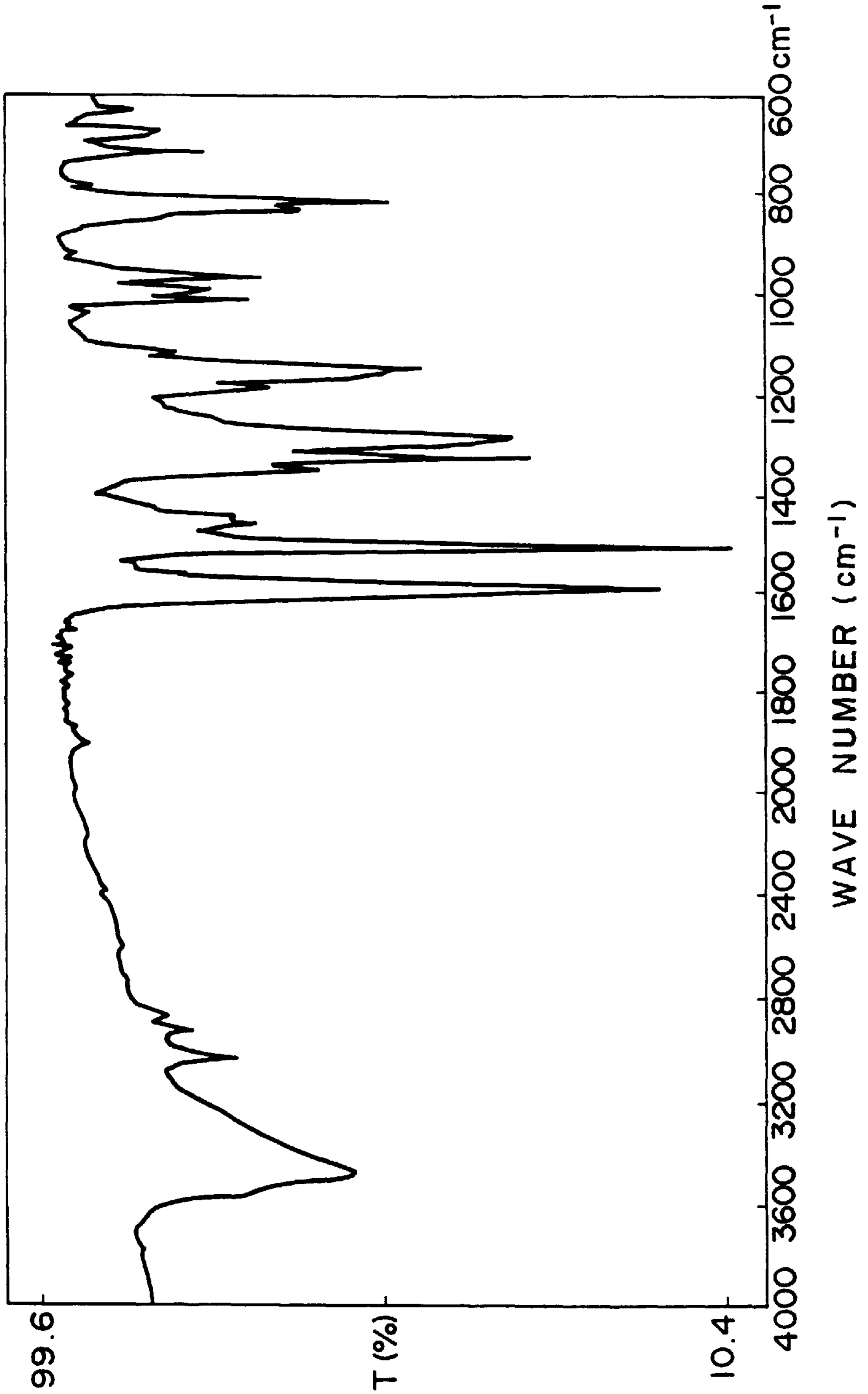

FIG. 3 shows an infrared spectrum of the stilbene product with the KBr method, indicating δCH (transolefin) at 965 $cm^{-1}$ and vsOH at 3,450 $cm^{-1}$.

EXAMPLE 3

Synthesis of N-(4-methylphenyl)-N-(1-pyrenyl)-4'-amino-3, 5-diacetoxystilbene (Compound No. 17):

Triphenyl-3,5-diacetoxybenzylphosphonium bromide (2.75 g (5.0 mmol)) and 0.60 g (15.0 mmol) of sodium hydride were added into 60 ml of tetrahydrofuran and stirred at room temperature for 2 hours. To the resulting mixture was added dropwise a solution of 2.06 g (5.0 mmol) of N-(4-formylmethyl)-N-(4-methylphenyl)-1-aminopyrene dissolved in 20 ml tetrahydrofuran over 30 minutes. The reaction mixture was then stirred at room temperature for 4 hours and poured in 600 ml of ice water. This was neutralized with hydrochloric acid and further stirred for 1 hour, followed by extraction with ethyl acetate. The extract was washed thrice with water, dried with magnesium sulfate and distilled under a reduced pressure to give a red oily product. This product was then mixed with 30 ml of acetic anhydride and 30 ml of toluene and the resulting mixture was refluxed for 4 hours. After being cooled to room temperature, the reaction mixture was extracted with toluene. The extract was washed with water, dried with magnesium sulfate and distilled to remove the solvent, thereby obtaining a red oily residue. The residue was separated, by silica gel column chromatography using a 20:1 (vol/vol) toluene/ethyl acetate mixed solvent as an elution liquid, into 1.5 gunreactecd aldehyde and 1.01 g (yield: 33.6%) of N-(4-methylphenyl)-N-(1-pyrenyl)-4'-amino-3,5-diacetoxystilbene in an amorphous form. The stilbene product was recrystallized from n-hexane to obtain 0.90 g (yield: 29.9%) of N-(4-methylphenyl)-N-(1-pyrenyl)-4'-amino-3 5-diacetoxystilbene as white yellow powder having a melting point of 185.5–188.5° C. The elementary analysis gave the following results:

| | C (%) | H (%) | N (%) |
|---|---|---|---|
| Calculated* | 81.84 | 5.19 | 2.33 |
| Found | 82.13 | 5.28 | 2.18 |

*as $C_{41}H_{31}NO_4$

Figure 4:
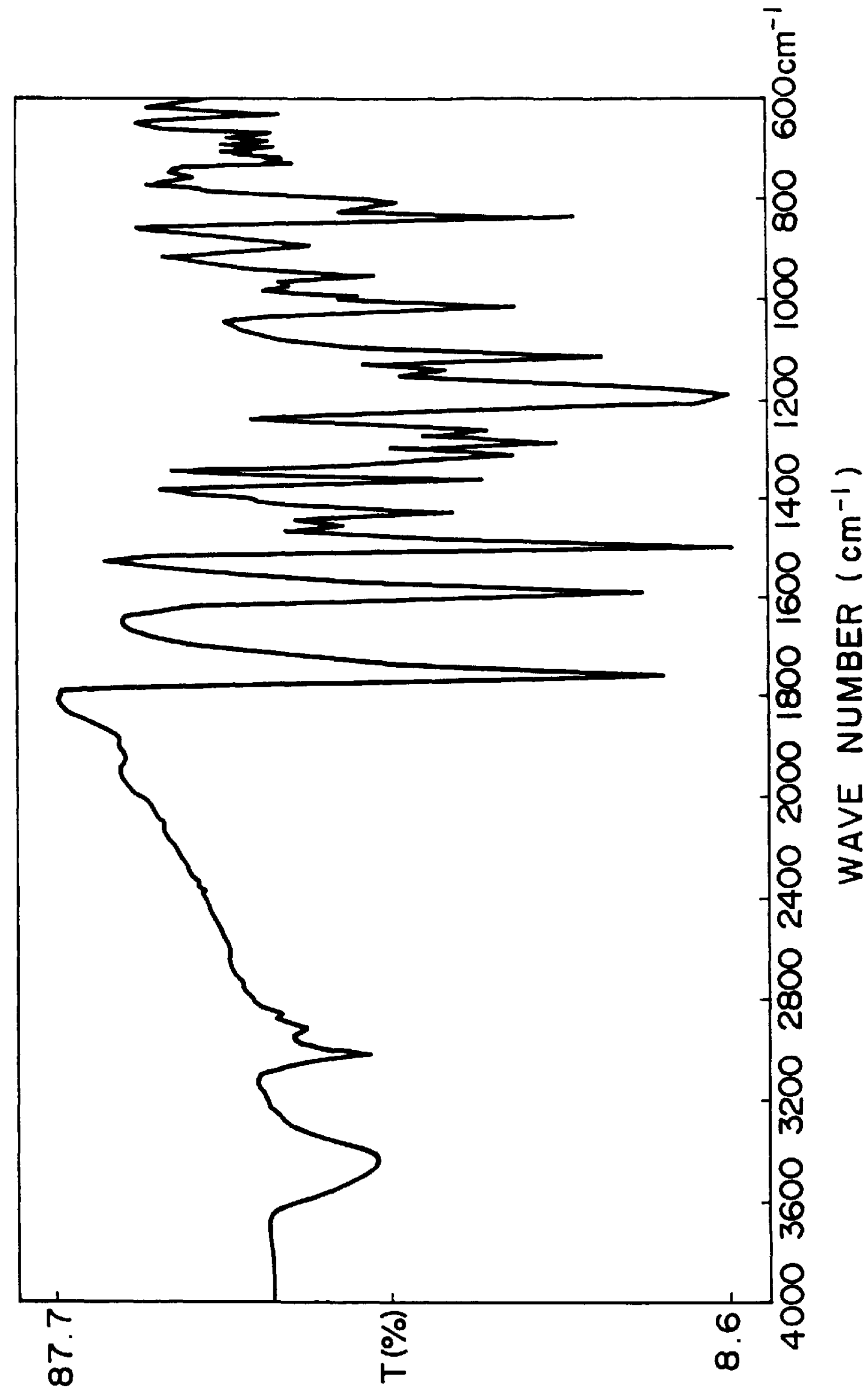

FIG. 4 shows an infrared spectrum of the stilbene product with the KBr method, indicating δCH (transolefin) at 965 $cm^{-1}$, VCOO at 1,195 $cm^{-1}$ and VCO at 1,765 $cm^{-1}$.

EXAMPLE 4

Synthesis of 4'-bis(4-methylphenyl)amino-3,5-dimethoxy-stilbene:

N,N-Bis(4-methylphenyl)-N-(4-formylphenyl)-amine (87.40 g (0.29 mol)) and 89.37 g (0.31 mol) of diethyl 3,5-dimethoxybenzylphosphate were added into 600 ml of N,N-dimethylformamide, to which were slowly added 51.61 g (0.46 mol) of potassium t-butoxide over 10 minutes with stirring. The resulting mixture was then reacted at room temperature for 3 hours. Thereafter, this was poured in 3,000 ml of ice water and the mixture was neutralized with acetic acid. The precipitates thus formed were recovered by filtration, washed with water and then with methanol, and dried to obtain 124.73 g (yield: 98.7%) of a crude product. The crude product was chromatographed on a silica gel column using a 3/2 (vol/vol) toluene/cyclohexane elution liquid. The product was further purified by recrystallization from an ethyl acetate/ethanol mixed solvent to obtain 108.43 g (yield: 85.8%) of 4'-bis(4-methylphenyl)amino-3,5-dimethoxystilbene as white yellow cubic crystals having a melting point of 135.5–136.5° C. The elementary analysis gave the following results:

| | C (%) | H (%) | N (%) |
|---|---|---|---|
| Calculated* | 82.73 | 6.71 | 3.22 |
| Found | 82.75 | 7.29 | 3.04 |

*as $C_{30}H_{29}NO_2$

The infrared spectrum of the thus obtained dimethoxystilbene with the KBr method was found to be identical with that of FIG. 2.

EXAMPLE 5

Synthesis of 4'-bis(4-methylphenyl)amino-3,5-diacetoxy-stilbene (Compound No. 16):

N,N-Bis(4-methylphenyl)-N-(4-formylphenyl)-amine (1.21 g (4.0 mmol)) and 1.65 g (4.8 mmol) of diethyl 3,5-diacetoxybenzylphosphate were added into 25 ml of dry tetrahydrofuran, to which were added 0.38 g (9.6 mmol) of sodium hydride. The resulting mixture was then reacted at room temperature for 36 hours. Thereafter, this was poured in 300 ml of ice water and the mixture was neutralized with acetic acid and extracted thrice with ethyl acetate. The extract was washed 6 times with water, dried with magnesium sulfate and distilled under vacuo to remove the solvent, thereby obtaining yellow brown oily product. This was chromatographed on a silica gel column using a 20/1 (vol/vol) toluene/ethyl acetate elution liquid. From the eluate, yellow powder was obtained. The product was further purified by recrystallization from n-hexane to obtain 0.11 g(yield: 5.6%) of 4'-bis(4-methylphenyl)amino-3,5-diacetoxystilbere as yellow crystals in the form of needles having a melting point of 122.5–123.5° C. The elementary analysis gave the following results:

| | C (%) | H (%) | N (%) |
|---|---|---|---|
| Calculated* | 78.18 | 5.95 | 2.85 |
| Found | 78.30 | 6.04 | 2.76 |

*as $C_{32}H_{29}NO_4$

Figure 5:
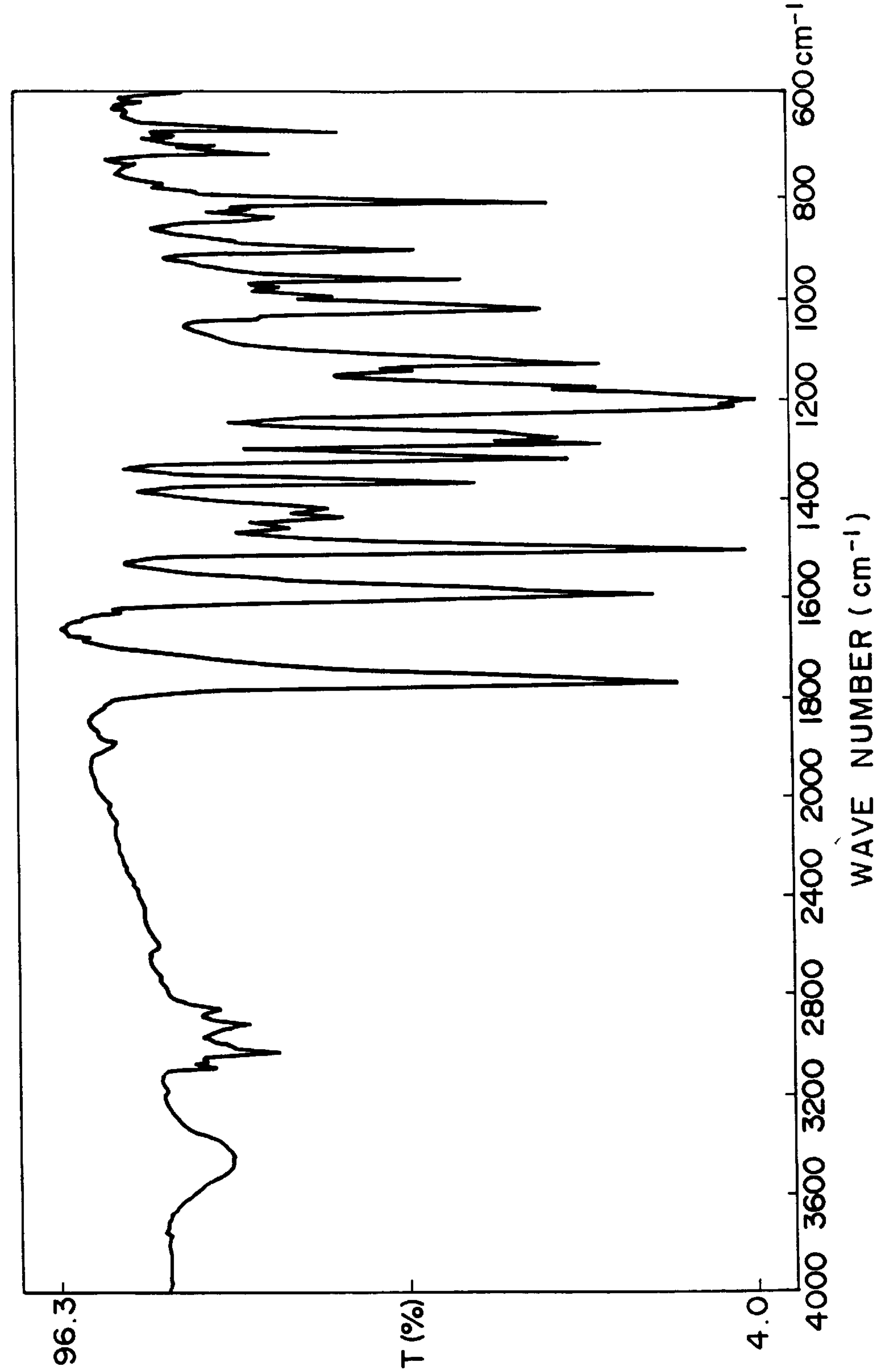

FIG. 5 shows an infrared spectrum of the thus obtained diacetoxystilbene with the KBr method, indicating δCH (transolefin) at 965 $cm^{-1}$ and νCO at 1, 770 $cm^{-1}$.

EXAMPLE 6

Synthesis of 4'-bis(4-methylphentl)amino-3,5-dihydroxy-stilbene (Compound No. 1):

N,N-Bis(4-methylphenyl) amino-3,5-diacetoxy-stilbene (0.36 g (0.7 mmol)) obtained in Example 5 was dissolved in 20 ml of methanol, to which 1.5 ml of 36% hydrochloric acid was added dropwise under reflux. The reaction was completed by 30 minutes stirring. The reaction mixture was then poured in 100 ml of water and extracted twice with ethyl acetate. The extract was washed thrice with water, dried with magnesium sulfate and chromatographed on a silica gel column using a 5/1 (vol/vol) toluene/ethyl acetate elution) liquid. From the eluate, 0.27 g (yield: 90.0%) of 4'-bis(4-methylphenyl)amino-3,5-dihydroxystilbene as yellow crystals in the form of needles having a melting point of 161.0–165.6° C. The elementary analysis gave the following results:

| | C (%) | H (%) | N (%) |
|---|---|---|---|
| Calculated* | 82.53 | 6.18 | 3.44 |
| Found | 82.67 | 6.27 | 3.32 |

*as $C_{28}H_{25}NO_2$

The infrared spectrum of the thus obtained dihydroxystilbene with the KBr method was found to be identical with that of FIG. 3.

EXAMPLE 7

Synthesis of 4'-bis(4-methylphenyl)amino-3-hydroxy-5-methoxystilbene (Compound No. 7):

4'-bis(4-methylphenyl)amino-3,5-dimethoxy-stilbene (31.07 g (71.34 =mol)) obtained in Example 4 was dissolved in 175 ml of N,N-dimethylformamide which had been treated with molecular sieves 4A, to which 20.00 g (214.01 mmol) of 90% sodium thioethalate were added. The resulting mixture was then reacted at 130° C. for 3 hours with stirring in a nitrogen gas stream. Thereafter, the reaction mixture was cooled to room temperature and poured in 1,500 ml of ice water, followed by addition of concentrated hydrochloric acid to make the liquid acidic. This was extracted twice with ether and the extract was distilled to remove the solvent. The residue was chromatographed on a silica gel column using a 5:1 (vol/vol) toluene/ethyl acetate mixed solvent as an elution liquid. From the eluate, 28.06 g (yield: 93.3%) of 4'-bis(4-methylphenyl)amino-3-hydroxy-5-methoxystilbene was obtained as yellow amorophous powder. The elementary analysis gave the following results:

| | C (%) | H (%) | N (%) |
|---|---|---|---|
| Calculated* | 82.63 | 6.46 | 3.32 |
| Found | 82.84 | 6.51 | 3.20 |

*as $C_{29}H_{27}NO_2$

Figure 6:
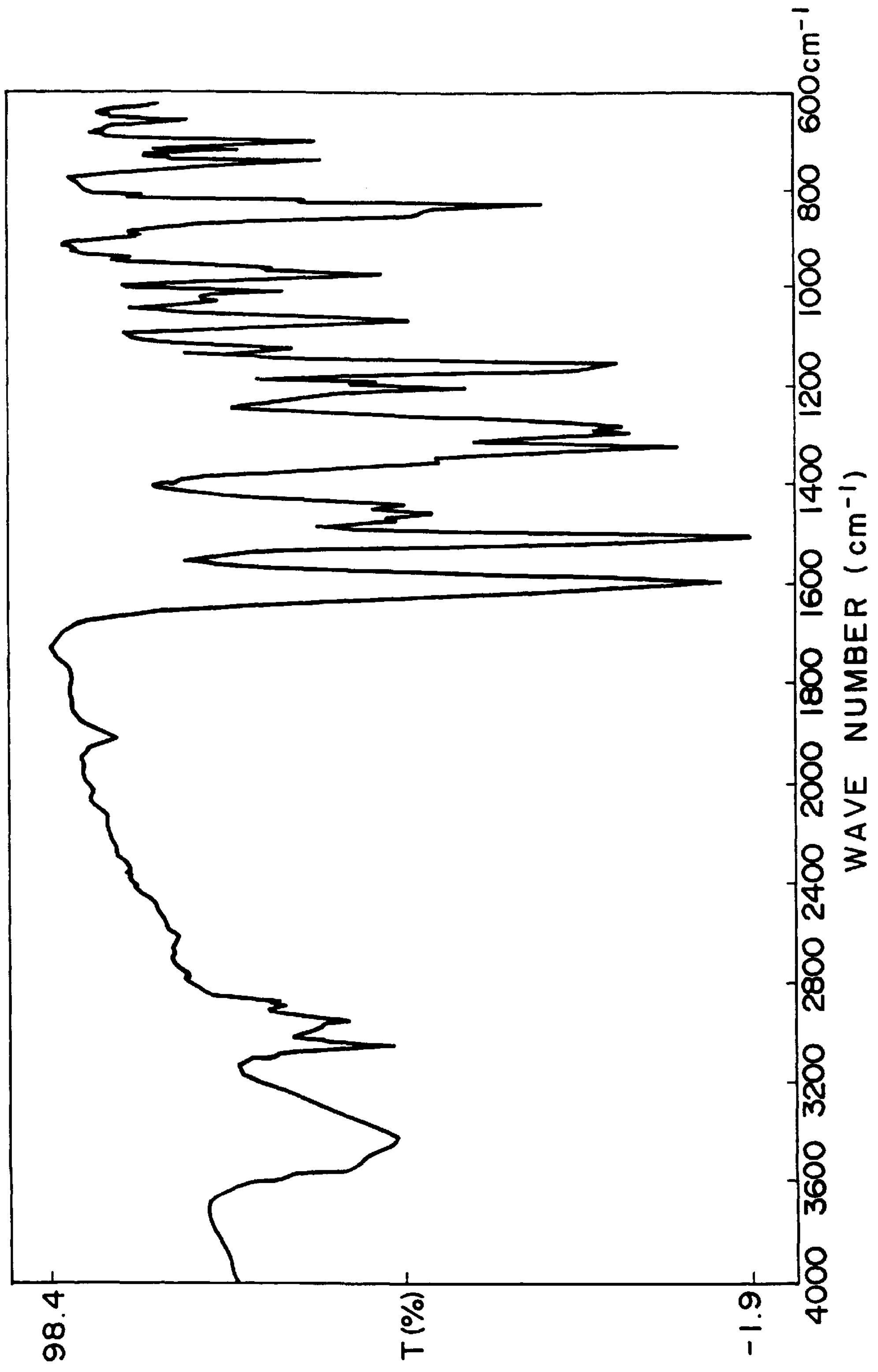

FIG. 6 shows an infrared spectrum of the stilbene product with the KBr method, indicating δCH (transolefin) at 960 $cm^{-1}$ and νsOH at 3440 $cm^{-1}$.

EXAMPLE 8

Preparation of Photoconductor No. 1:

Diane Blue (76 parts by weight, C.I. Pigment Blue 25, CI21180) serving as a charge generating material, 1,260 parts by weight of a 2% tetrahydrofuran solution of a polyester resin (Trademark “Vylon 200” made by Toyobo Company, Ltd.) and 3,700 parts by weight of tetrahydrofuran were dispersed and ground in a ball mill. The thus prepared dispersion was applied to an aluminum surface of an aluminum-deposited polyester film (electroconductive substrate) by a doctor blade, and dried at room temperature, so that a charge generation layer having a thickness of about 1 μm was formed on the electroconductive support.

Stilbene Compound No. 1 (2 parts by weight) in Table 1 prepared in Example 2, 2 parts by weight of a polycarbonate resin (Trademark “Panlite K-1300” made by Teijin Limited) and 16 parts by weight of tetrahydrofuran were mixed to form a coating solution for a charge transport layer. The coating solution was applied to the above charge generation layer by a doctor blade, and dried at 80° C. for 2 minutes and then at 120° C. for 5 minutes, so that a charge transport layer having a thickness of about 20 μm was formed on the charge generation layer. Thus, a two-layered electrophotoconductive photoconductor No. 1 according to the present invention was obtained.

EXAMPLES 9–53

Preparation of Photoconductors Nos. 2–46:

Example 8 was repeated in the same manner as described except that the combination of the charge generating and transport materials was varied as shown in Table 2, thereby obtaining electrophotographic photoconductors Nos. 2–46 according to the present invention were obtained.

TABLE 2
| Photoconductor No. | Charge Generating Material | Charge Transproting Material (Stilbene Compound No.) |
|---|---|---|
| 1 | 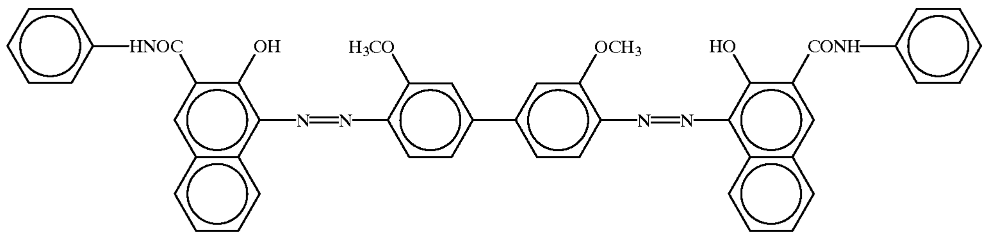 | 1 |
| 2 | 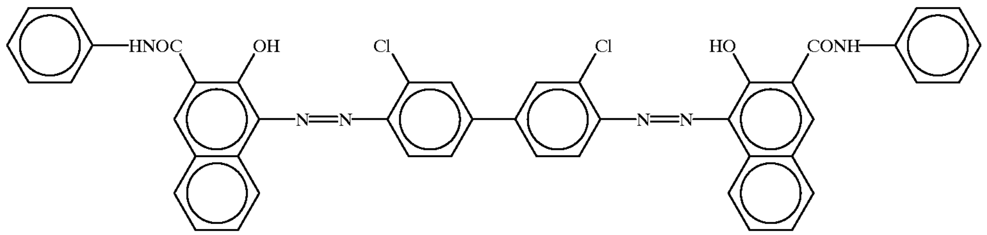 | 1 |
| 3 | 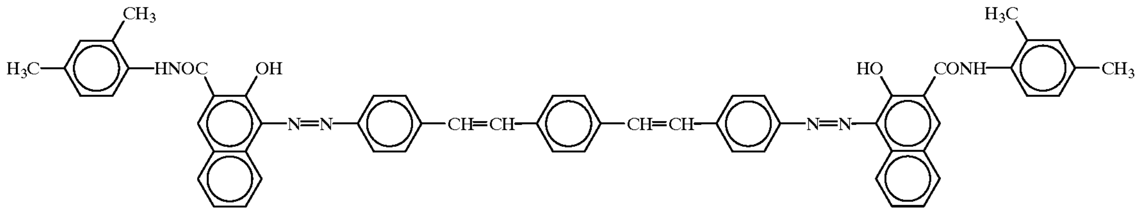 (hereinafter referred to as P-1.) | 1 |

TABLE 2-continued
| Photoconductor No. | Charge Generating Material | Charge Transproting Material (Stilbene Compound No.) |
|---|---|---|
| 4 | 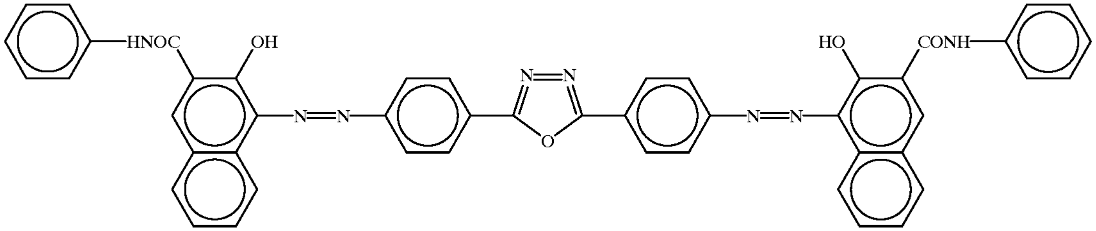 | 1 |
| 5 | 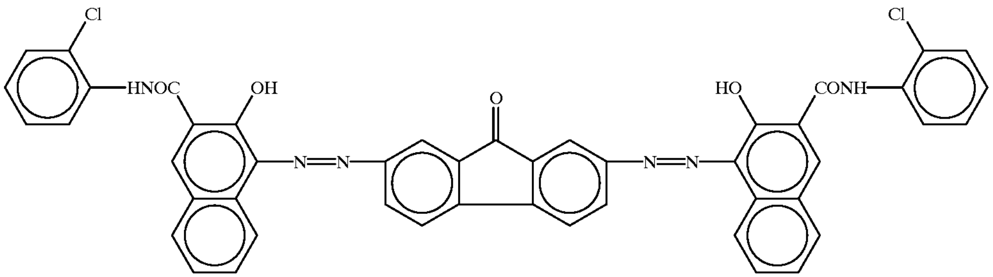 (hereinafter referred to as P-2.) | 1 |
| 6 | 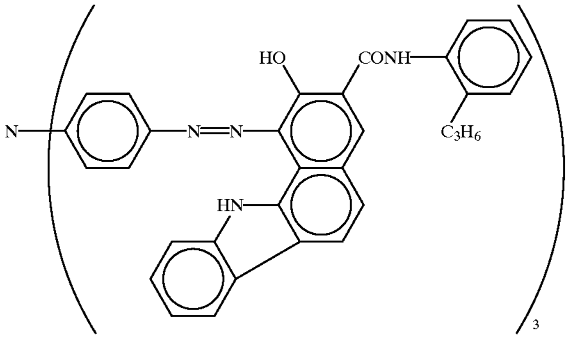 (hereinafter referred to as P-3.) | 1 |
| 7 | β-type Copper Phthalocyanine | 1 |
| 8 | P-1 | 5 |

TABLE 2-continued

| Photoconductor No. | Charge Generating Material | Charge Transproting Material (Stilbene Compound No.) |
|---|---|---|
| 9 | P-2 | 5 |
| 10 | P-3 | 5 |
| 11 | P-1 | 6 |
| 12 | P-2 | 6 |
| 13 | P-3 | 6 |
| 14 | P-1 | 7 |
| 15 | P-2 | 7 |
| 16 | P-3 | 7 |
| 17 | P-1 | 8 |
| 18 | P-2 | 8 |
| 19 | P-3 | 8 |
| 20 | P-1 | 10 |
| 21 | P-2 | 10 |
| 22 | P-3 | 10 |
| 23 | P-1 | 11 |
| 24 | P-2 | 11 |
| 25 | P-3 | 11 |
| 26 | P-1 | 13 |
| 27 | P-2 | 13 |
| 28 | P-3 | 13 |
| 29 | P-1 | 16 |
| 30 | P-2 | 16 |
| 31 | P-3 | 16 |
| 32 | P-1 | 17 |
| 33 | P-2 | 17 |
| 34 | P-3 | 17 |
| 35 | P-1 | 19 |
| 36 | P-2 | 19 |
| 37 | P-3 | 19 |
| 38 | P-1 | 20 |
| 39 | P-2 | 20 |
| 40 | P-3 | 20 |
| 41 | P-1 | 21 |
| 42 | P-2 | 21 |
| 43 | P-3 | 21 |
| 44 | P-1 | 34 |
| 45 | P-2 | 34 |
| 46 | P-3 | 34 |

EXAMPLE 54

Preparation of Photoconductor No. 47:

Onto an aluminum plate having a thickness of about 300 μm, selenium was vacuum-deposited to form a charge generating layer.

Stilbene Compound No. 1 (2 parts by weight) in Table 1 prepared in Example 2, 3 parts by weight of a polyester resin (Tradename "Polyester Adhesive 49000" made by Du Pont de Nemours, E. I. & Co.) and 45 parts by weight of tetrahydrofuran were mixed to form a coating solution for a charge transport layer. The coating solution was applied to the above charge generation layer by a doctor blade, and dried at room temperature and then under reduced pressure, so that a charge transport layer having a thickness of about 10 μm was formed on the charge generation layer. Thus, a two-layered electrophotoconductive photoconductor No. 47 according to the present invention was obtained.

EXAMPLE 55

Preparation of Photoconductor No. 48:

Example 54 was repeated in the same manner as described except that a perylene pigment of the formula shown below was substituted for selenium for the formation of the charge generating layer:

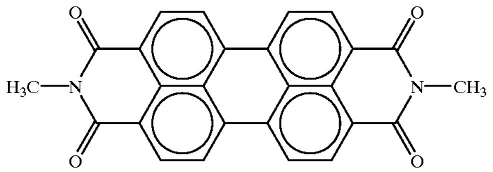

The charge generating layer of the photoconductor No. 48 had a thickness of about 0.6 μm.

EXAMPLE 56

Preparation of Photoconductor No. 49:

Diane Blue (1 part by weight, C.I. Pigment Blue 25, CI21180) and 158 parts by weight of tetrahydrofuran were dispersed and ground in a ball mill, to which 12 parts by weight of Stilbene Compound No. 1 in Table 1 and 18 parts by weight: of a polyester resin (Tradename "Polyester Adhesive 49000") were further added. The thus prepared dispersion was applied to an aluminum surface of an aluminum-deposited polyester film (electroconductive substrate) by a doctor blade, and dried at 100° C. for 30 minutes to form a photoconductive layer having a thickness of about 16 μm, thereby obtaining a electrophotoconductive photoconductor No. 49 according to the present invention.

EXAMPLE 57

Preparation of Photoconductor No. 50:

Stilbene Compound No. 1 (2 parts by weight) in Table 1, 2 parts by weight of a polycarbonaze resin (Trademark "Panlite K-1300" made by Teijin Limited) and 16 parts by weight of tetrahydrofuran were mixed to form a coating solution for a charge transport layer. The coating solution was applied to an aluminum surface of an aluminum-deposited polyester film by a doctor blade and dried at 80° C. for 2 minutes and then at 120° C. for 5 minutes, so that a charge transport layer having a thickness of about 20 μm was formed thereon. A mixture of 13.5 parts by weight of the bisazo pigment (P-2) shown in Table 2, 5.4 parts by weight of polyvinyl butyral (Tradename "XYHL" made by Union Carbide Japan K. K.), 680 parts by weight of tetrahydrofuran and 1020 parts by weight of ethyl cellosolve was dispersed and ground in a ball mill. To this dispersion, 1700 parts by weight of ethyl cellosolve were added to form a coating liquid for a charge generating layer. The coating liquid was applied to the charge transport layer by spray coating and dried at 100° C. for 10 minutes, so that a charge generating layer having a thickness of about 0.2 μm was formed on the charge transport layer. A solution of a polyamide resin (Tradename "CM-8000" Trade by Toray Silicone Co., Ltd.) in a mixed solvent of methanol and n-butanol was then applied on the charge generation layer by spray coating and dried at 120° C. for 30 minutes, so that a protective layer having a thickness of about 0.5 μm was formed thereon. Thus, an electrophotographic photoconductor No. 50 according to the present invention was obtained.

Electrophotographic Characteristics:

Each of the electrophotographic photoconductors Nos. 1–50 thus obtained was charged negatively or positively in the dark under application of −6 kV or +6 kV of corona charge for 20 seconds, using a commercially available electrostatic copying sheet testing apparatus ("Paper Analyzer Model SP-428" is made by Kawaguchi Electro Works Co., Ltd.). Each of the charged photoconductors was allowed to stand in the dark for 20 seconds without applying any charge thereto, and the initial surface potential Vpo (V) of the photoconductor was measured. Each photoconductor was then illuminated by a tungsten lamp such that the illuminance on the illuminated surface was 4.5 lux, and the time required for the initial surface potential Vpo (V) to reduce by half was measured. From the thus measured half-life, exposure $E_{1/2}$ (lux·sec) was calculated to give the results shown in Table 3.

Further, each of the electrophotographic photoconductors Nos. 1–50 was set in a commercially available electrophotographic copying machine, and the photoconductor was charged and exposed to light images via the original images to form latent electrostatic images thereon. The latent images were then developed into visible toner images by a dry developer, and the visible toner images were transferred to a sheet of plain paper and fixed thereon. As a result, clear toner images were obtained on the paper. When a wet developer was employed for the image formation, clear images were also formed on the paper.

TABLE 3

| Photoconductor No. | Vpo (V) | $E_{1/2}$ (lux · sec) |
|---|---|---|
| 1 | −1068 | 1.32 |
| 2 | −975 | 1.08 |
| 3 | −1002 | 1.05 |
| 4 | −1051 | 1.51 |
| 5 | −1037 | 0.97 |
| 6 | −437 | 0.59 |
| 7 | −1039 | 1.43 |
| 8 | −1153 | 0.98 |
| 9 | −1180 | 0.92 |
| 10 | −815 | 0.56 |
| 11 | −1123 | 1.15 |
| 12 | −1182 | 1.10 |
| 13 | −835 | 0.68 |
| 14 | −1100 | 1.05 |
| 15 | −1162 | 1.00 |
| 16 | −611 | 0.55 |
| 17 | −1186 | 1.00 |
| 18 | −1216 | 0.95 |
| 19 | −943 | 0.52 |
| 20 | −1005 | 1.09 |
| 21 | −994 | 1.07 |
| 22 | −1020 | 0.65 |
| 23 | −1015 | 1.04 |
| 24 | −1043 | 1.00 |
| 25 | −870 | 0.76 |

TABLE 3-continued

| Photoconductor No. | Vpo (V) | $E_{1/2}$ (lux · sec) |
|---|---|---|
| 26 | −1108 | 1.14 |
| 27 | −1115 | 1.0 |
| 28 | −1157 | 0.68 |
| 29 | −950 | 1.21 |
| 30 | −945 | 1.17 |
| 31 | −979 | 0.72 |
| 32 | −905 | 1.1 |
| 33 | −897 | 1.10 |
| 34 | −931 | 0.93 |
| 35 | −1080 | 1.12 |
| 36 | −1141 | 1.07 |
| 37 | −615 | 0.65 |
| 38 | −1263 | 1.07 |
| 39 | −1301 | 1.01 |
| 40 | −903 | 0.62 |
| 41 | −1221 | 1.15 |
| 42 | −1298 | 1.11 |
| 43 | −905 | 0.75 |
| 44 | −1015 | 1.11 |
| 45 | −1096 | 1.05 |
| 46 | −606 | 0.64 |
| 47 | −815 | 2.04 |
| 48 | −1026 | 2.91 |
| 49 | +1049 | 1.61 |
| 50 | +1054 | 1.02 |

Comparative Example 1

Example 8 was repeated in the same manner as described except that Diane Blue was replaced by charge generating material P-2 shown in Table 2 and that Stilbene Compound No. 1 was replaced by the following compound:

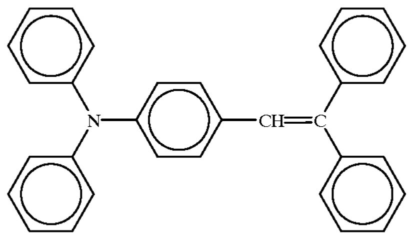

thereby to obtain a comparative photoconductor. The photoconductor was tested for the electrophotographic characteristics in the same manner as described above. As a result, the comparative photoconductor was found to show an initial surface potential Vpo of −1400 V and an exposure $E_{1/2}$ of 1.43 lux·sec.

The photoconductor according to the present invention not only gives excellent photoconductive properties but also shows high resistance to thermal and mechanical shocks. Additionally, the photoconductor can be fabricated at low costs. The novel stilbene compounds according to the present invention can be used as a raw material for a high molecular weight charge transport material.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A stilbene compound having the following formula (I):

(I)

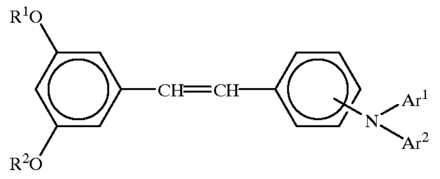

wherein $R^1$ and $R^2$ stand, independently from each other, for a hydrogen atom, an alkyl group which may have one or more substituents or an acyl group which may have one or more substituents and $Ar^1$ and $Ar^2$ stand, independently from each other, for a monovalent homocyclic aromatic group which may have one or more substituents with the proviso that at least one of $R^1$ and $R^2$ represents an acyl group.

2. A stilbene compound having the formula (I):

(I)

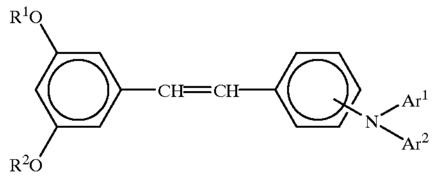

wherein $R^1$ and $R^2$ stand, independently from each other, for a hydrogen atom, an alkyl group which may have one or more substituents or an acyl group which may have one or more substituents and $Ar^1$ and $Ar^2$ stand, independently from each other for a monovalent homocyclic aromatic group which may have one or more substituents with the proviso that at least one of $R^1$ and $R^2$ represents a hydrogen atom or an acyl group; and wherein said monovalent homocyclic aromatic group is a biphenyl group.

3. A process for the production of a stilbene compound having the following formula (I):

(I)

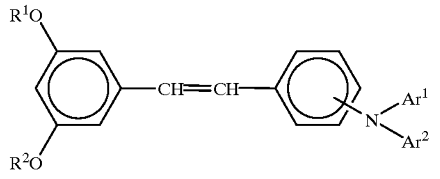

wherein $R^1$ and $R^2$ stand, independently from each other, for a hydrogen atom, an alkyl group which may nave one or more substituents or an acyl group which may have one or more substituents and $Ar^1$ and $Ar^2$ stand, independently from each other, for a monovalent homocyclic aromatic group which may haves one or more substituents, said process comprising reacting an aldehyde compound having the following formula (III):

(III)

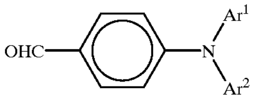

wherein $Ar^1$ and $Ar^2$ have the same meaning as above, with a phosphorus compound having the following formula (IV):

(IV)

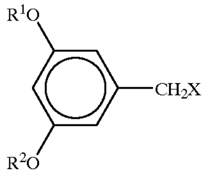

wherein $R^1$ and $R^2$ have the same meaning as above, X represents $-P^+(R^3)_3Y^-$ where $R^3$ represents a phenyl group or a lower alkyl group and Y represents a halogen atom.

4. A process as claimed in claim 3, wherein said stilbene compound obtained by said reaction and having the formula (I) in which $R^1$ and $R^2$ do not simultaneously represent a hydrogen atom is further subjected to a dealkylation or deacylation treatment to convert at least one of the $R^1O$ and $R^2O$ groups into a hydroxyl group.

5. A process for the production of a stilbene compound having the following formula (I):

(I)

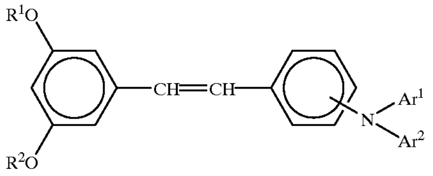

wherein $R^1$ and $R^2$ stand, independently from each other, for a hydrogen atom, an alkyl group which may have one or more substituents or an acyl group which may have one or more substituents and $Ar^1$ and $Ar^2$ stand, independently from each other, for a monovalent homocyclic aromatic group which may have one or more substituents, said process comprising reacting an amino compound having the following formula (V):

(V)

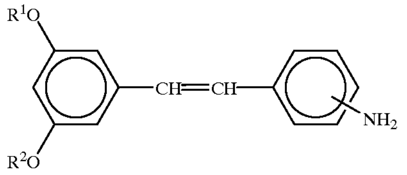

wherein $R^1$ and $R^2$ have the same meaning as above, with at least one of two halides having the following formulas (VI):

$Ar^1Z$ and $Ar^2Z$ (VI)

wherein $Ar^1$ and $Ar^2$ have the same meaning as above and Z represents a halogen atom.

6. A process as claimed in claim 5, wherein said stilbene compound obtained by said reaction and having the formula (I) in which $R^1$ and $R^2$ do not simultaneously represent a hydrogen atom is further subjected to a dealkylation or deacylation treatment to convert at least one of the $R^1O$ and $R^2O$ groups into a hydroxyl group.

7. A stilbene compound having the following formula (I):

(I)

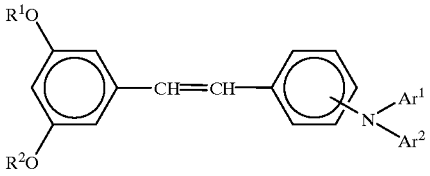

wherein $R^1$ and $R^2$ stand, independently from each other, for a hydrogen atom, a methyl group or an acyl group which may have one or more substituents and $Ar^1$ and $Ar^2$ stand, independently from each other, for a monovalent homocyclic aromatic group which may have one or more substituents with the proviso that at least one of $R^1$ and $R^2$ represents an acyl group.

* * * * *